US006911655B2

(12) United States Patent
Snowball (10) Patent No.: US 6,911,655 B2
(45) Date of Patent: Jun. 28, 2005

(54) FLUID TREATMENT APPARATUS

(76) Inventor: Malcolm Robert Snowball, "Woodside", 4 The Gables, The Plain, Epping, Essex CM16 6TW (GB)

( * ) Notice: Subject to any disclaimer, the term of this patent is extended or adjusted under 35 U.S.C. 154(b) by 0 days.

(21) Appl. No.: 10/458,874

(22) Filed: Jun. 11, 2003

(65) Prior Publication Data

US 2004/0036033 A1 Feb. 26, 2004

(30) Foreign Application Priority Data

Jun. 13, 2002 (GB) .............................................. 0213581
May 15, 2003 (GB) .............................................. 0311161

(51) Int. Cl.[7] .............................................. C02F 1/32
(52) U.S. Cl. ..................................................... 250/431
(58) Field of Search ............................... 250/436, 435, 250/438, 431, 432 R (56) References Cited

U.S. PATENT DOCUMENTS

| | | |
|---|---|---|
| 3,462,597 A | 8/1969 | Young |
| 6,013,917 A | 1/2000 | Ishiyama |
| 2001/0032659 A1 | 10/2001 | Wang et al. |

FOREIGN PATENT DOCUMENTS

| | | | |
|---|---|---|---|
| DE | 1283762 | | 11/1968 |
| DE | 3710250 A1 | | 10/1988 |
| DE | 19605311 C1 | * | 12/1996 |
| DE | 10032645 | | 1/2002 |
| JP | 10249334 A | | 9/1998 |
| JP | 2001170626 A | | 6/2001 |
| WO | WO 99/40032 | | 8/1999 |

OTHER PUBLICATIONS

European Patent Office Search Report dated Sep. 3, 2003.
United Kingdom Patent Office Search Report dated Sep. 23, 2003.

* cited by examiner

Primary Examiner—Kiet T. Nguyen
(74) Attorney, Agent, or Firm—Cook, Alex, McFarron, Manzo, Cummings & Mehler, Ltd.

(57) ABSTRACT

A fluid treatment apparatus comprises a plurality of elongate UV lamps 13 mounted in a duct 10 and a cleaning assembly 14 comprising a plurality of cleaning heads 20 which are rotated around respective lamps and are simultaneously driven longitudinally thereof to clean the lamps 13 and the internal surface of the duct 10. The cleaning heads 14 each comprise a plurality of portions 28 of titanium dioxide which are biased against the surface of the respective lamps 13 and which produce hydroxyls and oxygen free radicals in the presence of water and oxygen. Hydroxyls and oxygen free radicals are highly reactive and will break down the cells and molecules of the accumulated material on the lamps.

18 Claims, 6 Drawing Sheets

FIG. 7

# FLUID TREATMENT APPARATUS

BACKGROUND OF THE INVENTION

1. Field of the Invention

This invention relates to an apparatus for treating fluids and more particularly but not solely to an apparatus for disinfecting water.

2. Related Background Art

It is well known that high-intensity ultra-violet (UV) light has germicidal properties which can be used to sterilize water. EP-A-0202891 discloses a fluid treatment apparatus which utilizes these germicidal properties, and which comprises an elongate tubular duct having inlet and outlet ports at or adjacent its opposite ends, an elongate UV light source extending along the axis of the duct and a guide vane extending helically along the internal wall of the duct between the input and output ports.

Water treatment companies are reluctant to utilize UV sterilizers of the above-mentioned type because they do not effectively treat all of the water. One reason for this is that slime and other matter, which accumulates on the surface of the lamp submerged in the water, attenuates the UV light so much that micro-organisms which do not come within close proximity of the UV lamp do not receive a dose of UV radiation which is sufficient to kill them. Furthermore, the main accumulation on the lamp is attributable to the dead carcasses of micro-organisms: such carcasses undesirably act to filter a substantial amount of the UV light being transmitted.

In order to overcome the above-mentioned problems, fluid treatment apparatus are known which comprise a sleeve of polytetrafluoroethylene (PTFE), mounted as close but sliding fit on the elongate lamp. A piston can be actuated to occasionally drive the sleeve along the lamp, so as to clean the latter.

A disadvantage of this arrangement is that the sleeve actually smears the slime and other debris and in fact exacerbates the problem.

Another disadvantage of this arrangement is that the lamp may be slightly irregular in cross-section and thus there is a risk that the sleeve could miss the lamp, with the result that the lamp may not cleaned in some areas. There is also a risk that the sleeve could foul and break the lamp.

We have now devised a fluid treatment apparatus which alleviates the above-mentioned problems.

SUMMARY OF THE INVENTION

In accordance with this invention, there is provided a fluid treatment apparatus comprising a treatment chamber for receiving the fluid to be treated, an elongate source of electromagnetic radiation extending through said chamber for irradiating the fluid to be treated, said source of radiation being substantially circular in cross-section, and cleaning means mounted within the chamber, said cleaning means comprising a portion resiliently biased against the external surface of said radiation source and actuator means for rotating said portion circumferentially around said radiation source and for simultaneously driving the portion longitudinally of said radiation source.

In use, the portion of the cleaning means, which is biased against the external surface of the radiation source, is driven around the lamp and at the same time is driven longitudinally of the lamp. This creates a scrubbing action which substantially cleans any slime or other matter which may have accumulated on the surface of the lamp.

Any changes in the shape of the lamp along its length are accommodated by the resilient bias applied to the portion of the cleaning means. Thus, the risk of the lamp not being fully cleaned or damaged is avoided.

Preferably said cleaning means comprises a plurality of portions which are resiliently biased against the external surface of said radiation source.

In one embodiment, said portions of the cleaning means are provided by adjacent turns of an elongate helical coil spring having opposite ends which are brought together to form an annular ring around said radiation source, the spring being biased against the external surface of said radiation source.

Preferably, the internal diameter of the annular ring formed by the spring is less than the external diameter of said radiation source, so as to provide said resilient bias.

In an alternative embodiment, said portions of the cleaning means are provided by filaments arranged in a mesh or pad which is biased against the external surface of said radiation source.

Preferably, the or each said portion of the cleaning means comprises an outer surface of a photo catalytic oxidizing semiconductor material, which is preferably titanium dioxide.

When the titanium dioxide ($TiO_2$) or other photo catalytic oxidizing semiconductor is irradiated with UV light, its surface becomes activated and, in the presence of water and oxygen, produces hydroxyls and oxygen free radicals. Hydroxyls and oxygen free radicals are highly reactive and will break down the cells and molecules of the accumulated material on the lamp. In the case of micro-organisms, the hydroxyls and oxygen free radicals will destroy them by attacking and breaking down their cell walls.

Preferably the titanium dioxide is of the anatase form, which is the most reactive.

Preferably the cleaning means is formed of titanium, the titanium dioxide layer being formed by oxidizing the titanium in water or another chemical which more rapidly oxidizes the titanium. If any of the titanium dioxide layer becomes damaged during cleaning, the exposed titanium will slowly re-oxides in water to repair the damage.

Preferably, said radiation source comprises a lamp arranged to emit UV light, preferably having a wavelength below 400 nM.

Preferably means are provided for energizing said radiation source and for simultaneously activating said cleaning means.

Preferably said energizing and activating means comprises a sensor mounted remote from said radiation source which is arranged to provide an indication when the level of radiation falls below a predetermined value, thereby indicating that an accumulation of slime and other matter has developed.

Preferably the chamber comprises an elongate circular-section duct, the radiation source extending axially thereof.

In order to maximize the effect of the radiation, the internal wall of the duct is preferably reflective. It will be appreciated however that slime and other matter also builds up on the reflective internal wall of the duct, thereby reducing the effect of the radiation.

Thus, the cleaning means preferably comprises a further portion resiliently biased against the internal surface of the duct and actuator means for rotating said further portion circumferentially around the duct and for simultaneously driving the portion longitudinally of the duct.

Preferably, the cleaning means comprises a rotational shaft extending axially of the radiation source and which is arranged to rotate the or each of said actuator means and to drive the latter axially of the shaft.

Preferably the actuator means which drives the portion for cleaning the lamp comprises a sleeve mounted for rotation around the axis of said elongate radiation source.

Preferably the actuator means which drives the portion for cleaning the duct comprises a rotatable member mounted normal to the axis of the shaft rotation and having said portion on the radially outermost portion thereof.

Preferably the actuator means which drives the portion for cleaning the lamp is geared to the actuator means which drives the portion for cleaning the duct.

Preferably, the apparatus comprises a plurality of elongate radiation sources mounted parallel to each other, said cleaning means being arranged to clean each radiation source.

Preferably, each radiation source is arranged on a line which extends circumferentially of the shaft.

Preferably the portion for cleaning the duct comprises a cavity which faces the radiation source, the cavity being provided with an inlet for the introduction of cleaning fluid.

Preferably the cleaning means is arranged to induce a turbulent flow in the fluid. When not in use, the cleaning means can be positioned upstream of the radiation source to create a turbulent flow of fluid through the duct: this turbulent flow of fluid creates a scrubbing action which helps to remove any slime or other matter which may have built up. This turbulence also ensures that all of the water or other fluid being treated comes within close proximity of the radiation source during treatment.

The cleaning means can be positioned downstream of the radiation source in instances when a turbulent flow is not be required.

BRIEF DESCRIPTION OF THE DRAWINGS

Embodiments of this invention will now be described way of examples only and with reference to the accompanying drawings, in which.

DETAILED DESCRIPTION OF THE PREFERRED EMBODIMENTS

Figure 1:
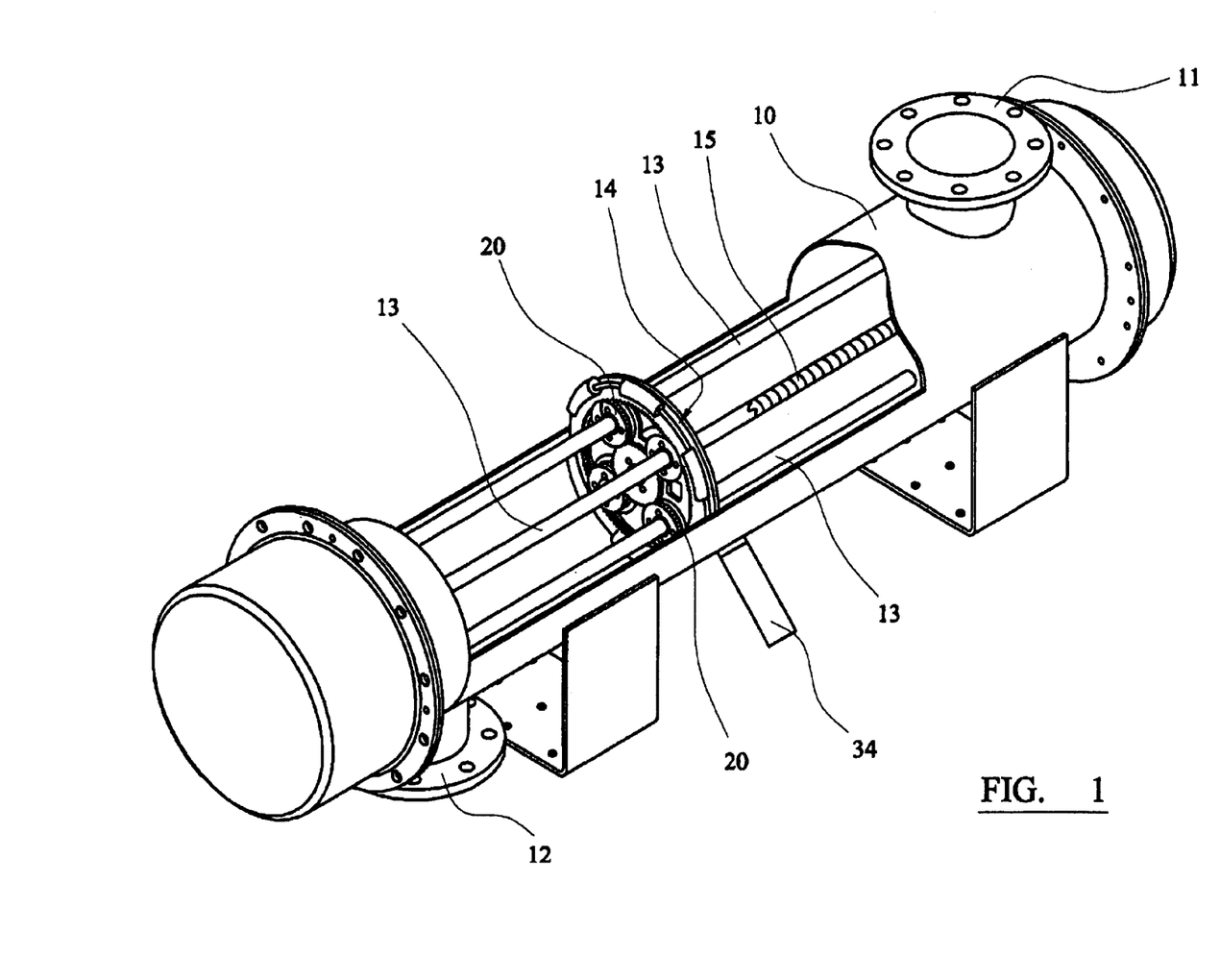
FIG. 1 is a perspective view of a first embodiment of water treatment apparatus in accordance with this invention, with some parts being shown cut away.

Referring to FIG. 1 of the drawings there is shown a water treatment apparatus comprising an elongate tubular duct 10 formed of stainless steel and having inlet and outlet ducts 11, 12 mounted at its opposite ends. Four parallel elongate ultra-violet lamps 13 extend along the axis of the duct 10.

In use, water flows through the duct 10 between the inlet 11 and outlet, where it is irradiated by the UV lamps 13. The lamps 13 illuminate and kill any micro-organisms in the water. However, the effectiveness of the apparatus depends on the dose of radiation received by the micro-organisms.

In time, slime and other matter, including the carcasses of dead micro-organisms accumulate on the lamps 13, as well as on the internal reflective surface of the duct 10. This accumulation of matter attenuates the UV light and can lead to an insufficient dose of radiation being delivered.

In order to overcome this problem, and in accordance with this invention, the apparatus further comprises a cleaning assembly 14 which is arranged to clean any matter which has accumulated from the surface of the lamps 13 as well as from the internal surface of the duct 10.

The cleaning assembly 14 is journalled to an elongate externally threaded screw-threaded shaft 15 which extends along the central axis of the duct 10, with each lamp 13 being circumferentially arranged around the shaft 15 at equal distances therefrom. A motor (not shown) at one end of the duct 10 rotates the shaft 15 about its axis, so as to drive the assembly along the duct in a direction according to the direction of shaft rotation.

Figure 2:
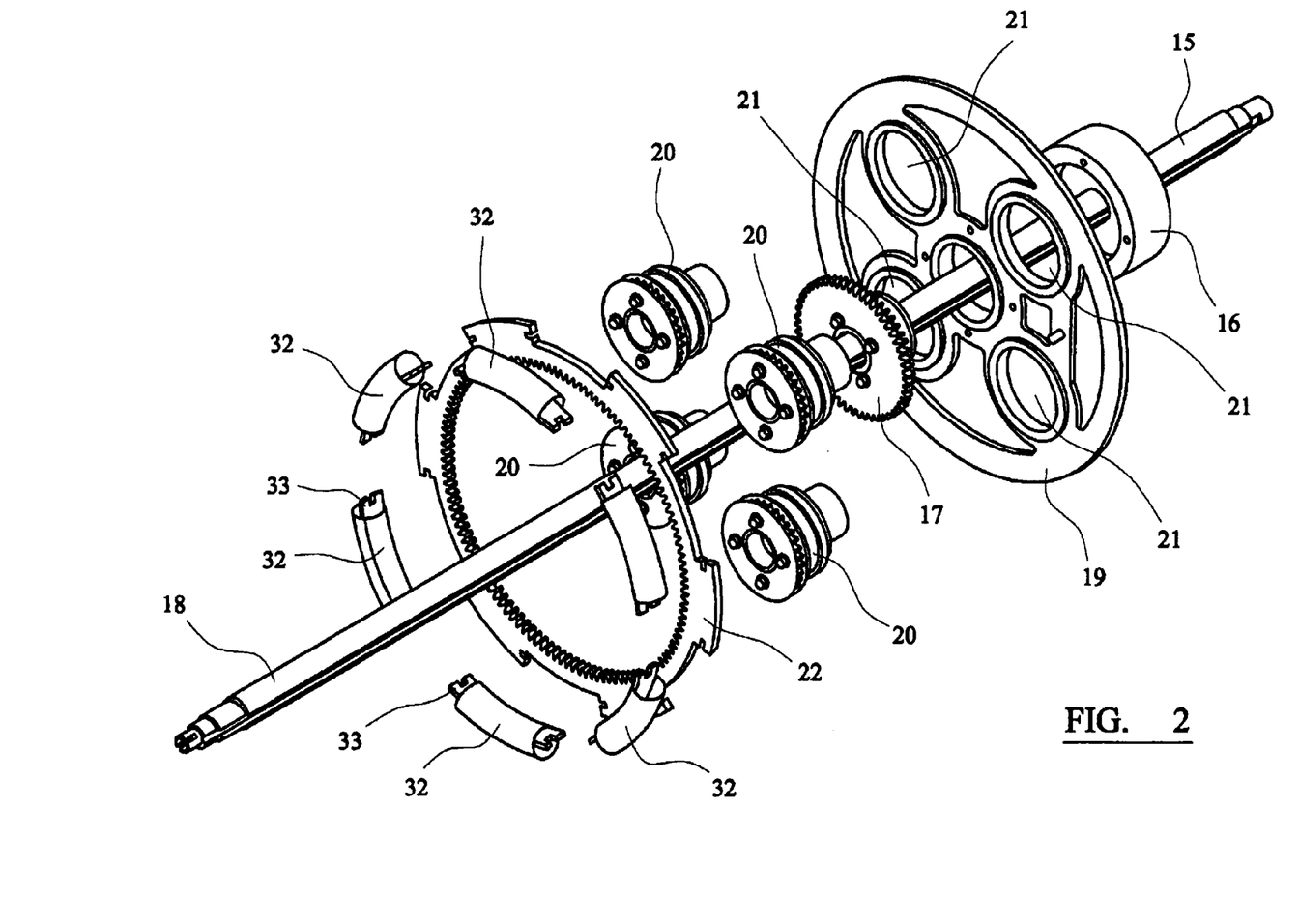
FIG. 2 is an exploded view of the cleaning assembly of the apparatus of FIG. 1.
Figure 3:
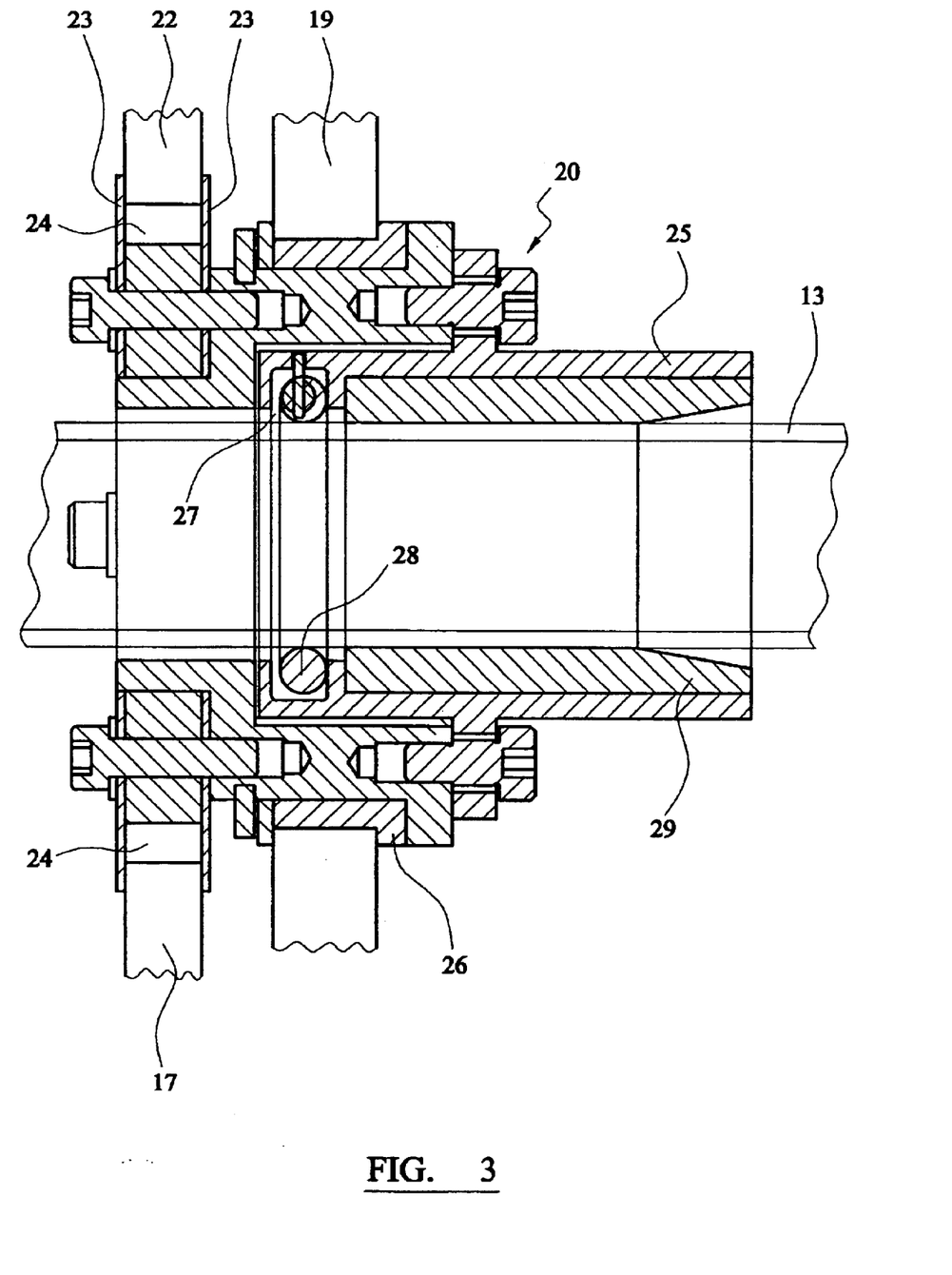
FIG. 3 is a longitudinal sectional view through the cleaning assembly of FIG. 2.

Referring to FIGS. 2 and 3 of the drawings, the cleaning assembly comprises an internally screw-threaded drive collar 16 mounted on the shaft 15. A drive gear 17 is also slidingly mounted on the shaft 15 and comprises a lug (not shown) which is received in a slot 18, which extends axially along the shaft 15. The drive gear 17 is captively but rotatably connected to the drive collar 16. A circular mounting plate 19 is fixed to the drive collar 15 and lies normal to the axis of the shaft 15.

The mounting plate 19 comprises a plurality of apertures 21, in which respective cleaning heads 20 are captively mounted for rotation about respective axes which extend parallel to the axis of the shaft 15.

Each cleaning head 20 comprises a through passage, through which a respective one of the lamps 13 extends. The cleaning heads 20 comprise a series of gear teeth 24 extending circumferentially thereof, which mesh with corresponding teeth formed on the drive gear 17.

The gear teeth 24 on the cleaning heads 20 also mesh with corresponding gear teeth that extend around the internal edge of an annular gear ring 22, which circumscribes the heads 20. The gear ring 22 is constrained against axial movement by flanges 23 disposed on opposite axial sides of the gear teeth 24 on each head 20.

In use, when the shaft 15 in rotated, the drive collar 16 (which is fixed against rotational movement by virtue of it being fixed to the mounting plate 19 that embraces the lamps 13) travels along the shaft 15 and carries with it the rest of the cleaning assembly 14.

The drive gear 17 is journalled to the slot 18 in the shaft 15 and thus the gear 17 turns as it is simultaneously driven along the shaft 15 by the drive collar 16.

As the drive gear 17 rotates, the cleaning heads 20, which are geared to the drive gear 17, also rotate about their respective lamps 13 as the assembly 14 travels along the shaft 15. Also, the gear ring 22 is rotated, by virtue of it being geared to the cleaning heads 20.

Each cleaning head 20 comprises a tubular body 25 mounted concentrically on its respective lamp 13 and attached to the mounting plate 19 by a bearing 26. The internal wall of the body 25 is formed with a circumferentially extending channel 27 at one end thereof, in which a cleaning spring 28 is seated. A further portion of the internal wall of the body 25 is also formed by a PTFE sleeve 29, which is preferably formed with a coarse internal screw thread.

Figure 4:
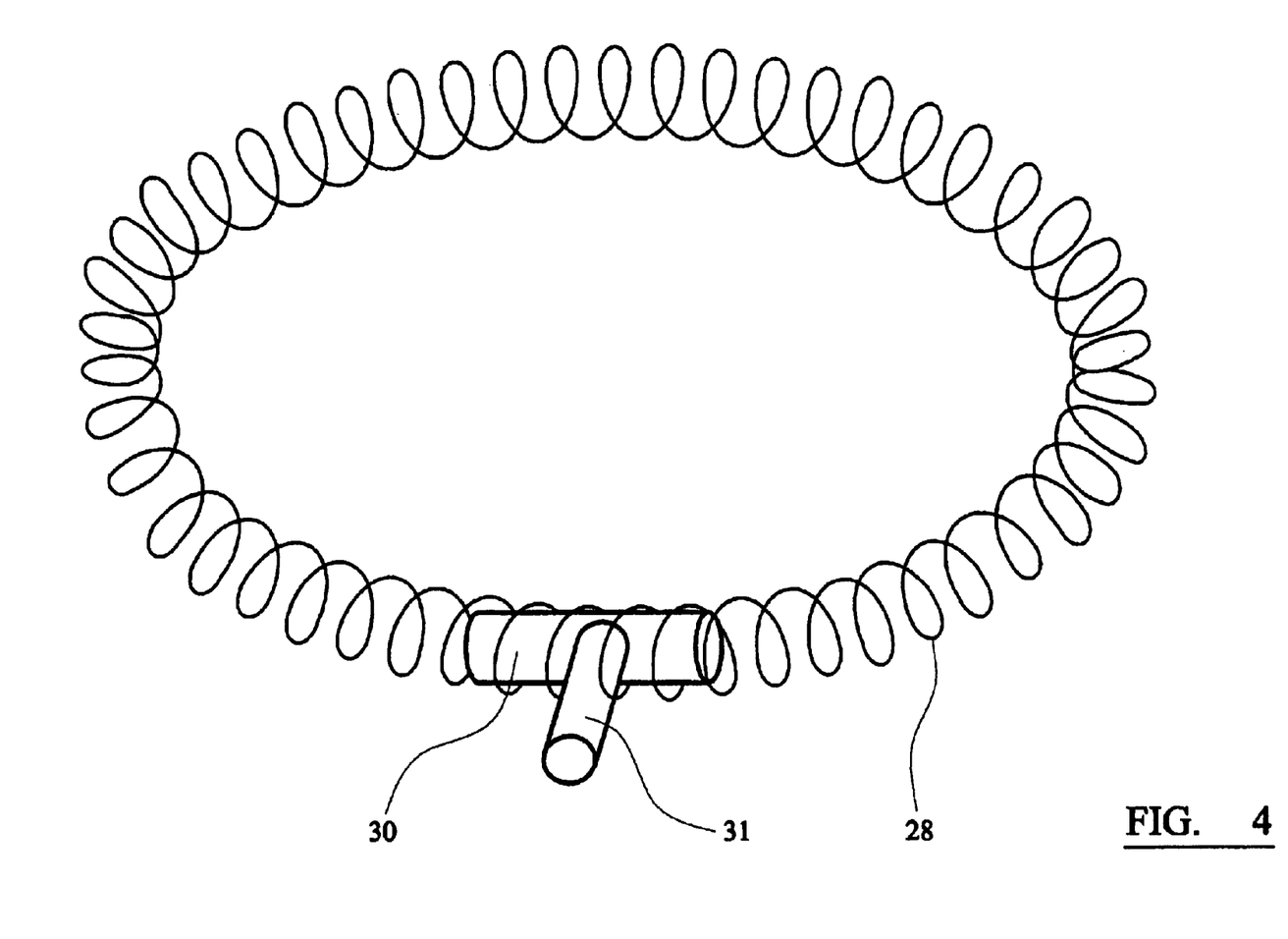
FIG. 4 is a perspective view of the cleaning spring of the cleaning assembly of FIG. 2.

Referring to FIG. 4 of the drawings, the spring 28 comprises an elongate helically wound coil spring of titanium wire, which is formed into an annulus by bringing its opposed ends together and inserting them onto the respective opposite ends of a short metal stud 30. A projection 31 extends radially outwardly of the annulus from the stud 30 and in use, this projection 31 is received in an aperture formed in the wall of the channel 27 of the body 20, so as to fix the spring relative to the body 20.

Referring again to FIG. 2 of the drawings, a plurality of further elongate titanium springs 32 are mounted axially on respective carriers 33, which extend circumferentially around the periphery of the gear ring 22.

In use, it will be appreciated that as the heads 20 rotate and advance along the lamps as hereinbefore described, the titanium springs 28 scour the surfaces of the lamps 13 and remove any matter which has accumulated thereon. Preferably the thread of the shaft 15 is fine so that the scoured portions of the lamp 13 on every turn of the head 20 are merged. The coarse internal screw thread on the PTFE sleeve 29 also acts as a scraper on the surface of the lamp 13 to further enhance the cleaning action.

The springs 32 around the gear ring 22 abut the internal wall of the duct 10 and act to scour the latter, thereby improving the reflectivity of the internal surface of the duct 10.

The cleaning is preferably performed when the duct 10 isolated from the fluid flow, so that the apparatus can be drained and flushed to remove all of the matter which has been cleaned from the surfaces of lamps 13 and duct 10.

During cleaning the lamps 13 are preferably illuminated to irradiate the titanium springs 28, 32, on which a layer of titanium dioxide is formed by pre-treating the titanium with an oxidizing chemical.

When the titanium dioxide is irradiated with UV light, its surface becomes activated and, in the presence of water and oxygen, produces hydroxyls and oxygen free radicals. Hydroxyls and oxygen free radicals. Hydroxyls and oxygen free radicals are highly reactive and will break down the cells and molecules of the accumulated material on the lamps 13 and duct 10. In the case of micro-organisms, the hydroxyls and oxygen free radicals will destroy them by attacking and breaking down their cell walls.

In order to provide an indication of when cleaning is required, a photodetector 34 (FIG. 1) may be provided to provide an indication of the level of UV light inside the duct 10. When the level falls below a predetermined value, the cleaning cycle can be initiated manually or perhaps automatically.

Figure 5:
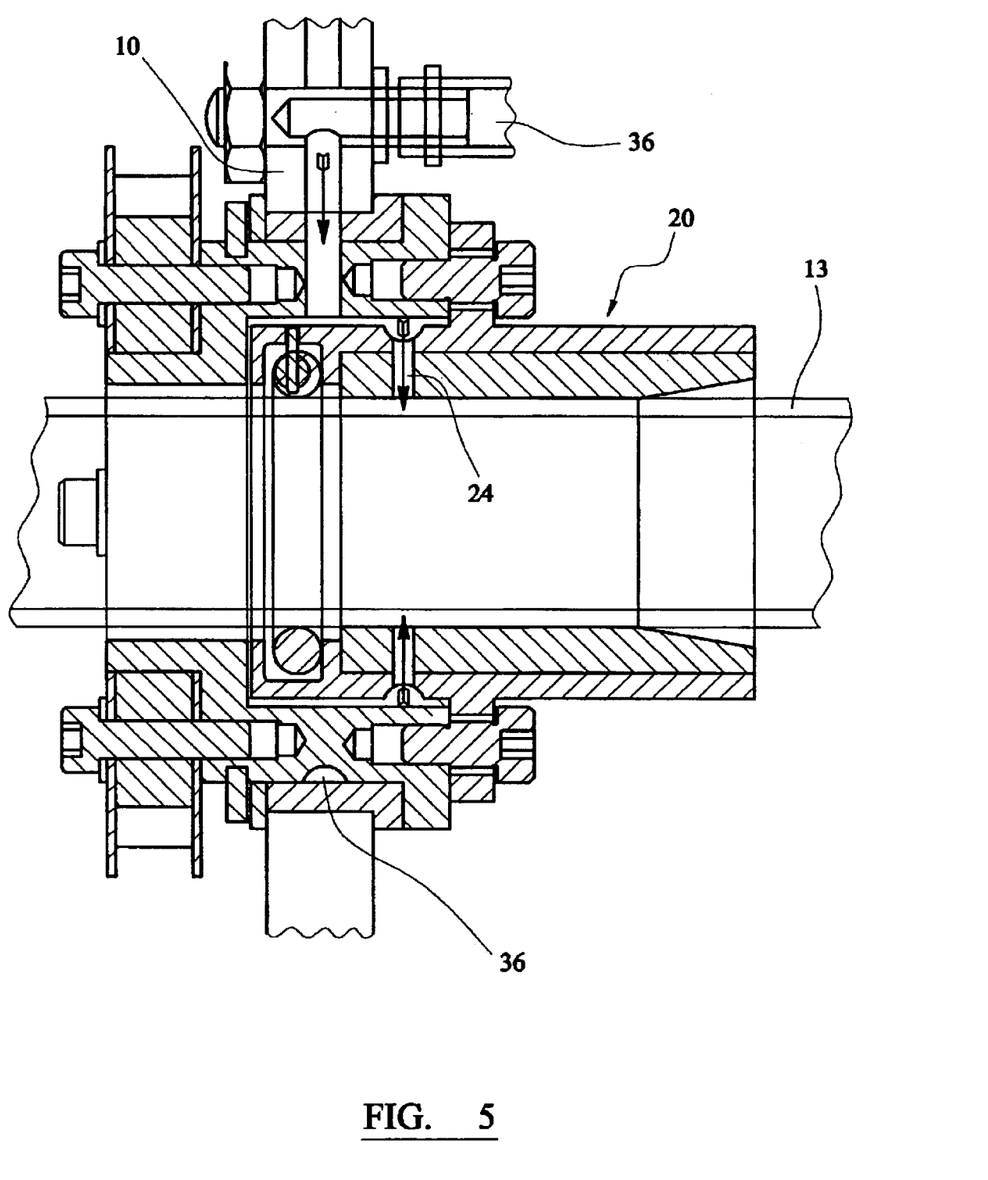
FIG. 5 is a longitudinal sectional view through the cleaning assembly of a second embodiment of water treatment apparatus in accordance with this invention.

If necessary a cleaning solution can be added to the water inside the duct during the cleaning cycle. Referring to FIG. 5 of the drawings, in an alternative embodiment, elongate extendable tubes 35 are connected to the mounting plate 19, to feed cleaning fluid into respective heads 20 by a rotational fluid coupling 36. Fluid is then conveyed through a passage 37 in the PTFE sleeve 29, so that the scraping action of the coarse thread inside the sleeve 29 is enhanced by the cleaning fluid.

The mounting plate 19 is arranged to induce a turbulent flow in the water. When not in use, the cleaning assembly 14 can be positioned upstream of the lamps 13, adjacent the inlet 11, to create a turbulent flow of fluid past the lamps 13: this turbulent flow of fluid creates a scrubbing action which helps to remove any slime or other matter which may have built up. This turbulence also ensures that all of the water being treated comes within close proximity of the lamps 13 during treatment.

The cleaning assembly 14 can be positioned downstream of the lamps 13 in instances when a turbulent flow is not be required.

Figures 6, 7:
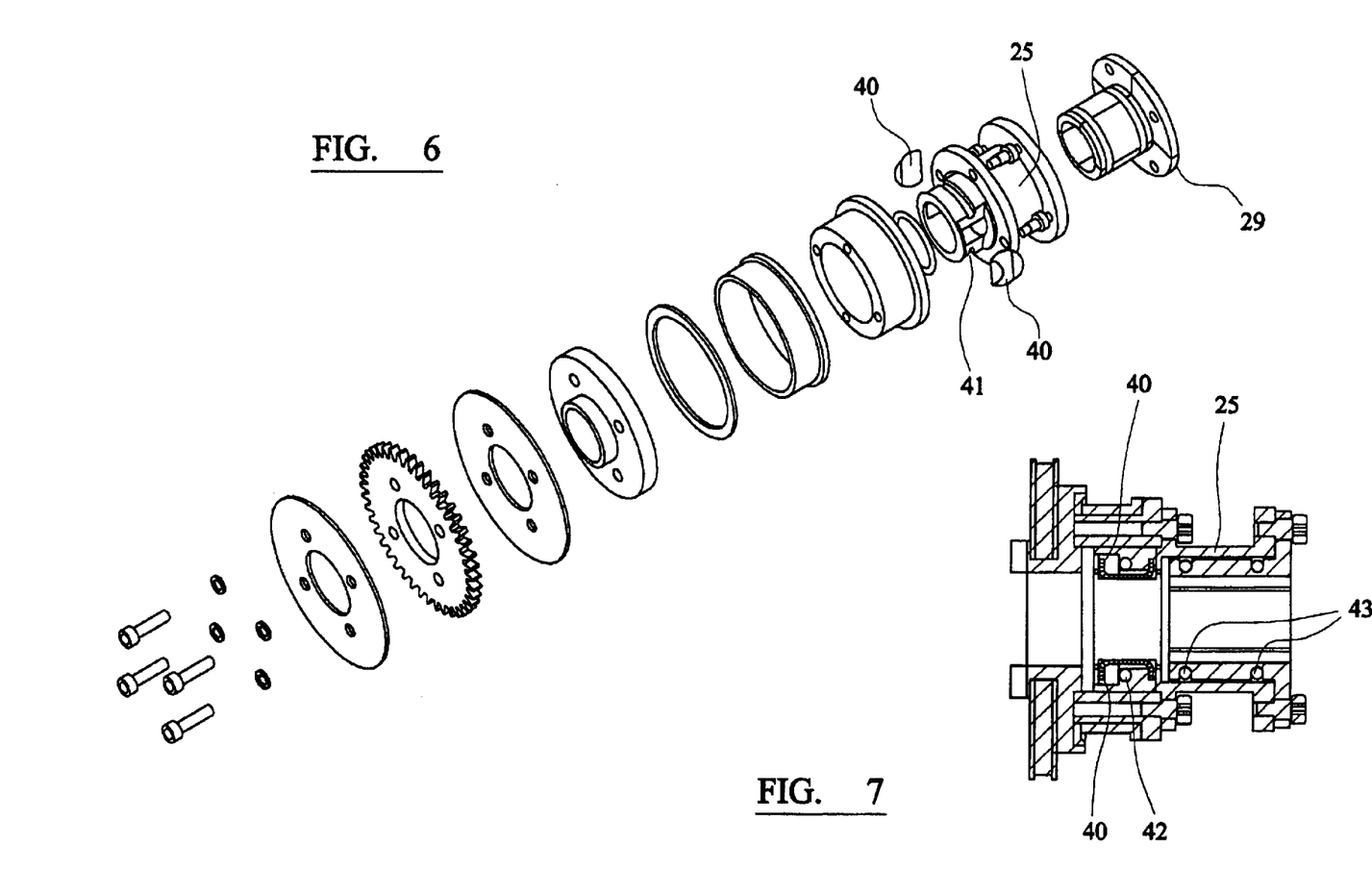
FIG. 6 is an exploded view of the cleaning assembly of a third embodiment of water treatment apparatus in accordance with this invention.
FIG. 7 is a sectional view through the cleaning assembly of the apparatus of FIG. 6.

Referring to FIGS. 6 and 7 of the drawings, in an alternative embodiment the titanium spring 28 is replaced by two mesh pads 40 of titanium wire, which are mounted in respective cut-outs 41 formed tangentially in the tubular body 25 of the cleaning head. The depth of the cut-outs 41 is greater than the wall thickness of the body 25 such that the surface of the lamp 13 is exposed in the cut-outs. A garter spring 42 extends around the body 25 and biases the mesh pads 40 against the exposed portions of the lamp surface.

Instead of being internally screw-threaded, the PTFE sleeve 29 is formed of four segments which are constrained against the lamp 13 by two garter springs 43. The radius of curvature of the internal surface of each segment is greater than the external diameter of the lamp 13, so that each segment contacts the lamp 13 along its longitudinal internal edges. The eight edges lie perpendicular to the direction of rotation and act to scrape the surface of the lamp 13.

A water treatment apparatus in accordance with this invention is extremely efficient at killing micro-organisms using UV light and does not suffer from a loss of performance, owing to the cleaning assembly which effectively removes slime and other accumulated matter on the surfaces of the lamps and duct.

While the preferred embodiments of the invention have been shown and described, it will be understood by those skilled in the art that changes of modifications may be made thereto without departing from the true spirit and scope of the invention.

I claim:

1. A fluid treatment apparatus comprising a treatment chamber for receiving the fluid to be treated, an elongate source of electromagnetic radiation extending through said chamber for irradiating the fluid to be treated, said source of radiation being substantially circular in cross-section, and cleaning means mounted within the chamber, said cleaning means comprising a portion resiliently biased against the external surface of said radiation source and actuator means for rotating said portion circumferentially around said radiation source and for simultaneously driving the portion longitudinally of said radiation source.

2. A fluid treatment apparatus as claimed in claim 1, in which said cleaning means comprises a plurality of portions which are resiliently biased against the external surface of said radiation source.

3. A fluid treatment apparatus as claimed in claim 2, in which said portions of the cleaning means are provided by adjacent turns of an elongate helical coil spring having opposite ends which are brought together to form an annular ring around said radiation source, the spring being biased against the external surface of said radiation source.

4. A fluid treatment apparatus as claimed in claim 3, in which the internal diameter of the annular ring formed by the spring is less than the external diameter of said radiation source, so as to provide said resilient bias.

5. A fluid treatment apparatus as claimed in claim 2, in which said portions of the cleaning means are provided by filaments arranged in a mesh or pad which is biased against the external surface of said radiation source.

6. A fluid treatment apparatus as claimed in claim 1, in which the or each said portion of the cleaning means comprises an outer surface of a photo catalytic oxidizing semiconductor material.

7. A fluid treatment apparatus as claimed in claim 6, in which the photo catalytic oxidizing semiconductor material comprises titanium dioxide.

8. A fluid treatment apparatus as claimed in claim 7, in which the titanium dioxide is of the anatase form.

9. A fluid treatment apparatus as claimed in claim 7, in which the cleaning means is formed of titanium, the titanium dioxide layer being formed by oxidizing the titanium.

10. A fluid treatment apparatus as claimed in any claim 1, in which said radiation source comprises a lamp arranged to emit UV light.

11. A fluid treatment apparatus as claimed in claim 1, in which means are provided for energizing said radiation source and for simultaneously activating said cleaning means.

12. A fluid treatment apparatus as claimed in claim 11, in which said energizing and activating means comprises a sensor mounted remote from said radiation source which is arranged to provide an indication when the level of radiation falls below a predetermined value.

13. A fluid treatment apparatus as claimed in claim 1, in which the chamber comprises an elongate circular-section duct, the radiation source extending axially thereof.

14. A fluid treatment apparatus as claimed in claim 1, in which the internal wall of the duct is reflective.

15. A fluid treatment apparatus as claimed in claim 1, in which the cleaning means comprises a further portion resiliently biased against the internal surface of the duct and means for rotating said further portion circumferentially around the duct and for simultaneously driving said further portion longitudinally of the duct.

16. A fluid treatment apparatus as claimed in claim 1, in which the cleaning means comprises a rotational shaft extending axially of the radiation source and which is arranged to rotate said actuator means and to drive the latter axially of the shaft.

17. A fluid treatment apparatus as claimed in claim 1, in which the cleaning means comprises a sleeve mounted for rotation around the axis of said elongate radiation source.

18. A fluid treatment apparatus as claimed in claim 1, in which the cleaning means comprises a cavity which faces the radiation source, the cavity being provided with an inlet for the introduction of cleaning fluid.

* * * * *